(12) United States Patent
Eskuri

(10) Patent No.: US 8,574,170 B2
(45) Date of Patent: Nov. 5, 2013

(54) GUIDEWIRE

(75) Inventor: Alan Eskuri, Irvine, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/441,116

(22) Filed: Apr. 6, 2012

(65) Prior Publication Data
US 2013/0267934 A1 Oct. 10, 2013

(51) Int. Cl.
*A61B 5/00* (2006.01)
(52) U.S. Cl.
USPC .............................................. 600/585
(58) Field of Classification Search
USPC .............................................. 600/585
See application file for complete search history.

(56) References Cited

U.S. PATENT DOCUMENTS

| | | | | |
|---|---|---|---|---|
| 4,827,941 A | * | 5/1989 | Taylor et al. | 600/434 |
| 5,238,005 A | * | 8/1993 | Imran | 600/585 |
| 5,243,996 A | * | 9/1993 | Hall | 600/585 |
| 5,271,415 A | * | 12/1993 | Foerster et al. | 600/585 |
| 5,406,960 A | * | 4/1995 | Corso, Jr. | 600/585 |
| 5,409,015 A | * | 4/1995 | Palermo | 600/585 |
| 5,636,641 A | | 6/1997 | Fariabi | |
| 5,636,642 A | | 6/1997 | Palermo | |
| 5,664,580 A | * | 9/1997 | Erickson et al. | 600/585 |
| 5,769,796 A | | 6/1998 | Palermo et al. | |
| 6,059,738 A | | 5/2000 | Stoltze et al. | |
| 6,113,557 A | * | 9/2000 | Fagan et al. | 600/585 |
| 6,387,060 B1 | | 5/2002 | Jalisi | |
| 6,390,993 B1 | * | 5/2002 | Cornish et al. | 600/585 |
| 6,482,166 B1 | | 11/2002 | Fariabi | |
| 6,508,803 B1 | | 1/2003 | Horikawa et al. | |
| 6,602,207 B1 | | 8/2003 | Mam et al. | |
| 6,666,829 B2 | | 12/2003 | Cornish et al. | |
| 6,679,853 B1 | | 1/2004 | Jalisi | |
| 7,182,735 B2 | * | 2/2007 | Shireman et al. | 600/585 |
| 7,540,845 B2 | | 6/2009 | Parins | |
| 7,637,875 B2 | | 12/2009 | Itou | |
| 7,641,622 B2 | | 1/2010 | Satou et al. | |
| 7,717,864 B1 | | 5/2010 | Grandfield et al. | |
| 7,878,985 B2 | | 2/2011 | Cornish et al. | |
| 7,905,003 B2 | | 3/2011 | Jalisi | |
| 7,972,283 B2 | | 7/2011 | Cornish et al. | |
| 2009/0157050 A1 | | 6/2009 | Fujimagari et al. | |
| 2009/0312670 A1 | | 12/2009 | Elsesser | |
| 2010/0036312 A1 | | 2/2010 | Krolik et al. | |

FOREIGN PATENT DOCUMENTS

EP   2 316 519 A1   5/2011

OTHER PUBLICATIONS

The European Search Report for EP 13 15 7645, dated May 23, 2013, 7 pages.

* cited by examiner

*Primary Examiner* — Max Hindenburg
(74) *Attorney, Agent, or Firm* — Elizabeth A. O'Brien Esq (57) ABSTRACT

A guidewire comprising an elongate guide member dimensioned for insertion within a body vessel of a subject is disclosed. The guide member defines a longitudinal axis and has trailing and leading end segments. The leading end segment has a reduced cross-sectional dimension relative to a cross-sectional dimension of the trailing end segment. The leading end segment includes at least one finger thereon. A first transverse dimension of the finger is greater than a corresponding first transverse dimension of the leading end segment in contact therewith.

29 Claims, 5 Drawing Sheets

GUIDEWIRE

BACKGROUND

1. Technical Field

The present disclosure generally relates to medical devices, and, in particular, relates to an intravascular guidewire for assisting in placement of an intravascular device within the neurovasculature for facilitating diagnostic and/or therapeutic neurovascular procedures.

2. Description of Related Art

Guidewires are commonly used in medical procedures to assist in the advance and proper positioning of a catheter or other medical device in lumens, vessels, or other cavities of the body. Neurovascular procedures utilizing guidewires include the imaging and treatment of aneurysms, arteriovenous malformations (AVM), and ischemic stroke. The effectiveness of an intravascular guidewire in advancing through tortuous neurovasculature without undesired deformation or kinking is dependent upon a number of factors and design considerations. These factors include, inter alia, the material(s) of fabrication of the guidewire, guidewire dimensions and intended use. Generally, a balance must be achieved to provide the required torsional, lateral, tensile and/or column strengths to enable easy and precise manipulation and steerability in the tortuous vasculature. Guidewires for such endovascular procedures face additional challenges due to the relatively small diameter required to navigate through the narrow and remote locations of the neurovasculature.

SUMMARY

Accordingly, the present disclosure is directed to a guidewire capable of accessing distal reaches of the vasculature, including the neurovasculature, while exhibiting sufficient torsional and lateral stiffness to enable steering of the guidewire through these tortuous regions. What is also desired is a guidewire having a distal end with improved tensile and torsional integrity, yet with the capability to readily bend in any direction.

In accordance with one embodiment of the present disclosure, a guidewire comprising an elongate guide member dimensioned for insertion within a body vessel of a subject. The guide member defines a longitudinal axis and has trailing and leading end segments. The leading end segment has a reduced cross-sectional dimension relative to a cross-sectional dimension of the trailing end segment. The leading end segment includes at least one finger thereon. A first transverse dimension of the finger is greater than a corresponding first transverse dimension of the leading end segment in contact therewith.

In disclosed embodiments, the leading end segment includes at least two fingers axially spaced along the leading end.

In disclosed embodiments, the two fingers include a different transverse dimension from each other.

In disclosed embodiments, a second transverse dimension of the at least one finger is substantially equal to a corresponding second transverse dimension of the leading end segment.

In disclosed embodiments, the leading end segment and the fingers are made of the same material.

In disclosed embodiments, a length of each finger along the first transverse axis is between about 0.002 inches and about 0.004 inches. Here, it is disclosed that a width of the leading end segment along the first transverse axis is between about 0.001 inches and about 0.002 inches. It is further disclosed that the width of each finger along the second transverse axis is between about 0.003 inches and about 0.025 inches. The leading end segment may include at least two fingers axially spaced along the leading end and the distance between adjacent fingers may be between about 0.010 inches and about 0.100 inches.

In disclosed embodiments, the ratio between a length of the finger along the first transverse axis and a width of the leading end segment along the first transverse axis is about 2:1.

In disclosed embodiments, the at least one finger extends through a radial center of the leading end segment. It is further disclosed that the leading end segment and/or at least one finger may define a polygonal cross-section.

In disclosed embodiments, a distal-most end of the distal-most finger is positioned proximally of a distal-most end of the leading end segment.

In disclosed embodiments, the leading end segment includes a pair of lateral sides disposed parallel to the longitudinal axis, and at least one finger projects laterally beyond each of the lateral sides of the leading end segment.

In disclosed embodiments, the leading end segment and the fingers are monolithically formed.

In disclosed embodiments, the guidewire further comprises an intermediate segment positioned between the leading end segment and the trailing end segment. The intermediate segment has a cross-sectional dimension that is larger than the cross-sectional dimension of the leading end segment and that is smaller than the cross-sectional dimension of the trailing end segment.

In accordance with another embodiment of the present disclosure, a method for manufacturing a surgical guidewire dimensioned for insertion within a body vessel of a subject is disclosed. The method comprises forming a guide member defining a longitudinal axis and having trailing and leading end segments. The leading end segment includes a reduced cross-sectional dimension relative to a cross-sectional dimension of the trailing end segment. The leading end segment includes at least one finger thereon. A first transverse dimension of the at least one finger is greater than a corresponding first transverse dimension of the leading end segment in contact therewith.

In disclosed embodiments, the leading end segment and the at least one finger are formed via micro machining or via stamping.

BRIEF DESCRIPTION OF THE DRAWINGS

Embodiments of the present disclosure will be readily appreciated by reference to the drawings wherein.

DESCRIPTION

In the following description, the terms "proximal" and "distal" as used herein refer to the relative position of the guidewire in a lumen. The "proximal" or "trailing" end of the guidewire is the guidewire segment extending outside the body closest to the clinician. The "distal" or "leading" end of the guidewire is the guidewire segment placed farthest into a body lumen from the entrance site.

The guidewire of the present disclosure has particular application in a neurovascular procedure, but may be used in any interventional, diagnostic, and/or therapeutic procedure including coronary vascular, peripheral vascular, and gastrointestinal applications in addition to a neurovascular application.

In the figures below, the full length of the guidewire is not shown. The length of the guidewire can vary depending on the type of interventional procedure, though typically it ranges in length from 30 centimeters to 400 centimeters (cm). Common lengths of guidewires for coronary, peripheral and neurovascular procedures may range from 170 cm to 300 cm in length. These lengths permit the use of standardized rapid exchange or over-the-wire catheter systems. The length of the shaped distal end also may vary, for example, from about 5 cm to about 80 cm in length.

In accordance with one application of the present disclosure, the maximum outer diameter of the guidewire ranges from about 0.008 inches to about 0.035 inches, standard for guidewires used in a neurovascular procedure. The diameter of the guidewire may remain relatively constant over a major portion of the length of the guidewire; however, the leading or distal end incorporates a generally tapered or narrowed configuration to permit flexure while navigating the tortuous vasculature.

The various embodiments of the disclosure will now be described in connection with the figures. It should be understood that for purposes of better describing the disclosure, the figures may not be to scale. Further, some of the figures include enlarged or distorted portions for the purpose of showing features that would not otherwise be apparent.

Figure 1:
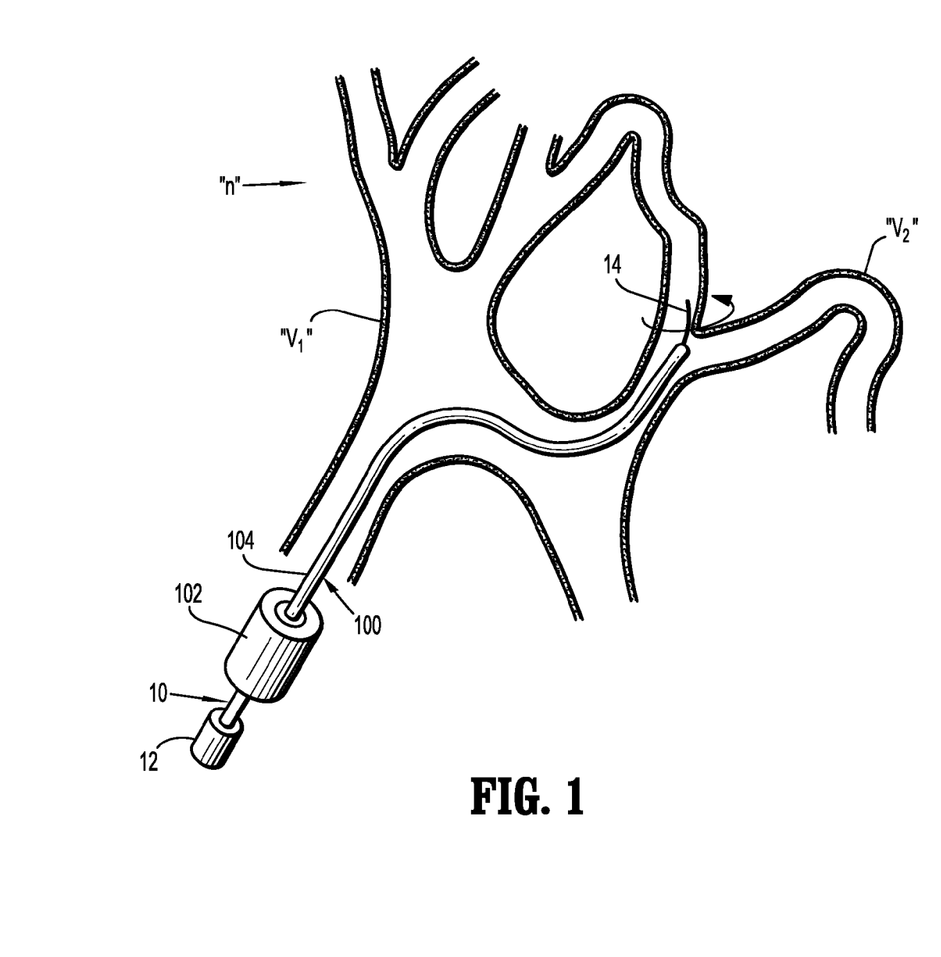
FIG. 1 is a perspective view of a guidewire and catheter in use within a tortuous region of the vasculature of a patient in accordance with the principles of the present disclosure.

Referring now to FIG. 1, a tortuous vasculature such as within the neurovascular space "n" is illustrated. For illustrative purposes, a tortuous path or a tortuous region within, e.g., the neurovascular space "n," includes large vasculature "$V_1$" and smaller branch vessels "$V_2$" which branch or extend from more proximal vessels at various angles, including up to 90 degrees or even greater than 90 degrees.

In FIG. 1, guidewire 10 of the present disclosure is illustrated as being positioned within a conventional access or microcatheter 100. Such microcatheters are known in the art. Commercially available microcatheters include Echelon™, Marathon™, and Nautica™ microcatheters sold by Tyco Healthcare Group LP dba Covidien, Irvine, Calif. In general, microcatheter 100 includes handle 102 and hollow catheter member 104 extending from the handle 102. Microcatheter 100 defines a longitudinal opening extending at least through catheter member 104 for passage or reception of guidewire 10.

Guidewire 10 includes actuator 12 and guide member 14 extending from the actuator 12. Actuator 12 may incorporate various features including handles, slides or the like, to facilitate handling and/or movement of guide member 14. For example, actuator 12 may be used to translate and/or rotate guide member 14 during placement within the vasculature.

Figure 2:
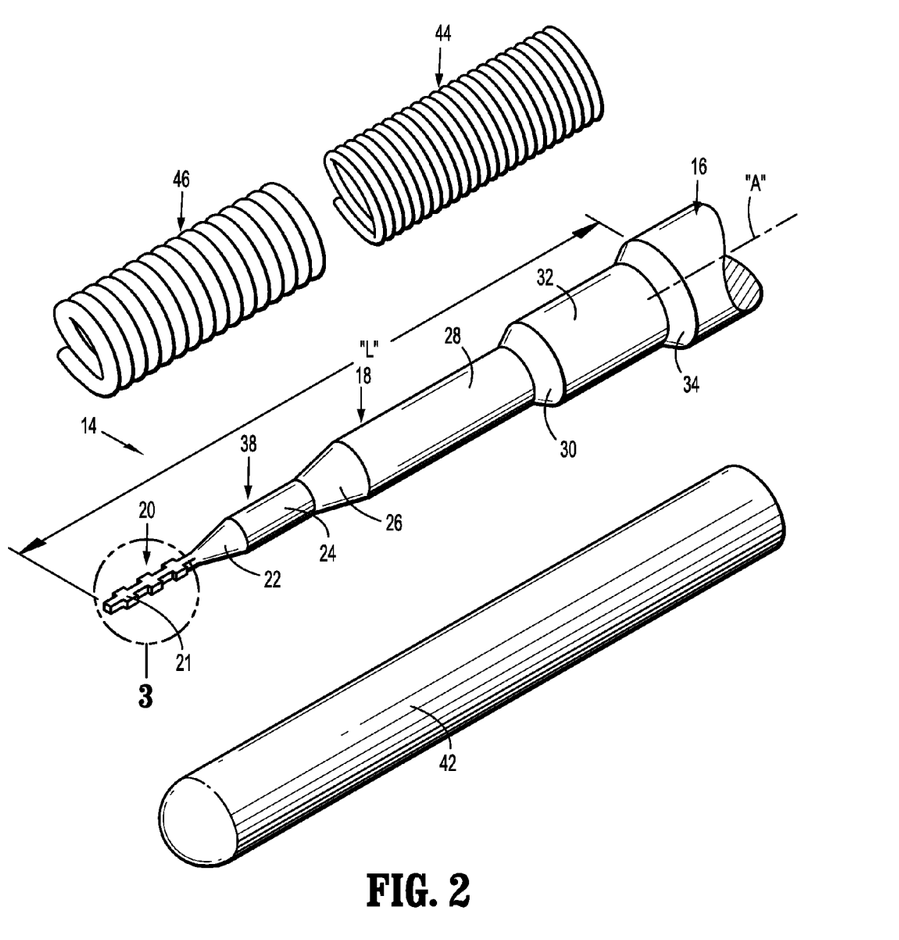
FIG. 2 is a perspective view with parts separated of the guidewire of FIG. 1 illustrating the guide member, support coils and outer sheath.

Referring now to FIG. 2, guide member 14 of guidewire 10 is illustrated and will be discussed in greater detail. Guide member 14 is dimensioned for insertion within the vasculature. Guide member 14 defines longitudinal axis "A" and has proximal or trailing end segment 16, and distal or leading end segment 18 forward of the trailing end segment 16. In FIG. 2, a major longitudinal portion of proximal end segment 16 is removed for ease of illustration. Trailing end segment 16 may be generally circular in cross-section with a length ranging from about 20 cm to about 240 cm, for example. Trailing end segment 16 may have a constant cross-sectional dimension or diameter along its length.

Figure 3:
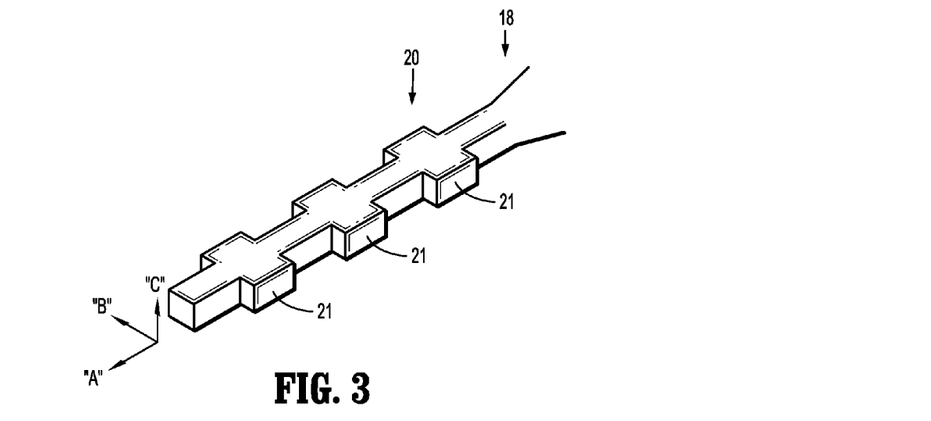
FIG. 3 is a perspective view of a portion of a leading end segment of the guide member of the guidewire of FIGS. 1 and 2.
Figure 7:
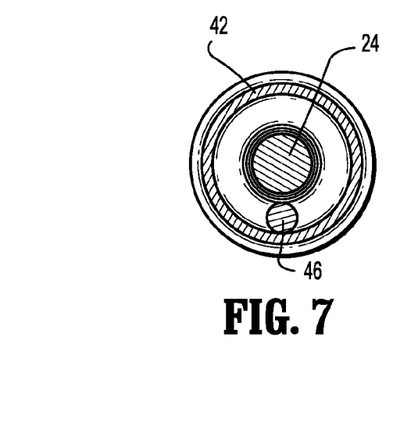
FIG. 7 is a transverse cross-sectional view of the guidewire of FIG. 6 taken along line 7-7.
Figure 8:
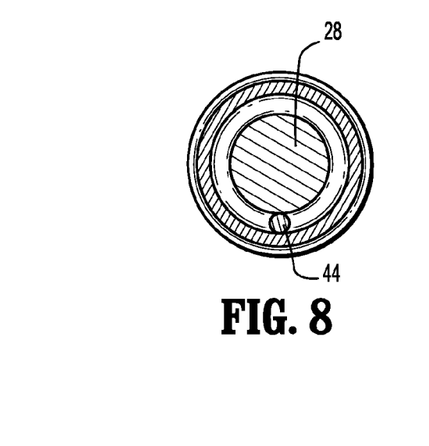
FIG. 8 is a transverse cross-sectional view of the guidewire of FIG. 6 taken along line 8-8.
Figure 9:
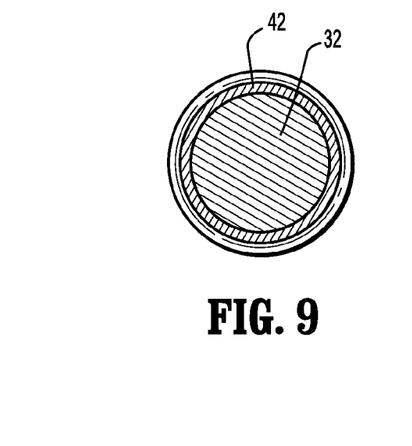
FIG. 9 is a transverse cross-sectional view of the guidewire of FIG. 6 taken along line 9-9.

With reference now to FIGS. 2-3, leading end segment 18 of guide member 14 forms the working end or tip of the guidewire 10 and defines a reduced cross-sectional dimension relative to the cross-sectional dimension of proximal end segment 16. The overall length "L" (FIG. 2) of leading end segment 18 may range from about 20 cm to about 60 cm depending on the maximum diameter (e.g., the diameter of proximal end segment 16) and the overall length of guidewire 10. Leading end segment 18 may include a number of alternating tapered and annular segments which generally increase in cross-sectional dimension or diameter from the extreme remote or distal end toward the proximal end, i.e., toward proximal end segment 16. In the embodiment of FIGS. 2-3, leading end segment 18 includes a distal remote segment 20, a first tapered segment 22 extending proximally from distal remote segment 20 and coterminous therewith, a first generally annular segment 24 extending from the first tapered segment 22 and coterminous therewith, a second tapered segment 26 extending from the first generally annular segment 24 and coterminous therewith, and a second generally annular segment 28 extending from the second tapered segment 26 and being coterminous therewith. Leading end segment 18 may further include a third tapered segment 30 extending contiguously from second annular segment 28 and a third annular segment 32 which is coterminous with the third tapered segment 30. As a further alternative, leading end segment 18 may also include a fourth tapered segment 34 extending from third annular segment 32 to leading end segment 16. First, second and third annular segments 24, 28, 32 may define circular cross-sections with various diameters as depicted in the cross-sectional views of FIGS. 7, 8 and 9, respectively. Suitable diameters of each of annular first second and third annular segments 24, 28, 32 for specific guidewire sizes will be provided hereinbelow. Tapered segments 22, 26, 30 and 34 are in oblique relation to the longitudinal axis "A." Tapered segments 22, 26 may define an angle relative to longitudinal axis "A" ranging from about 5 degrees to about 30 degrees. Tapered segments 30, 34 may define a greater angle relative to longitudinal axis "A," e.g., ranging from about 20 degrees to about 70 degrees.

While the present disclosure identifies several remote segments 20, 20a, 20b, and 20c, reference number 20 is intended to include each remote segment 20, 20a, 20b, and 20c. Additionally, while the present disclosure identifies several variations of fingers 21, 21a, 21b and 21c, reference number 21 is intended to include each variation of finger 21.

Remote segment 20 may define various configurations. In the embodiment of FIGS. 2-6 and 10-12, remote segment 20 is a flattened, planar or ribbon tip. However, remote segment 20 may define alternative cross-sectional shapes including circular, oval or the like. As a further alternative, remote segment 20 may be heat set into a variety of configurations including a linear arrangement. In one embodiment, remote segment 20 is heat set to maintain, e.g., a non-linear configuration such as a curve, by subjecting the remote segment 20 to heat at about 500° C. to about 525° C. for a duration of time ranging from about 30 seconds to about 2 minutes. Remote segment 20 may also be provided with a bent "j-hook" as is known in the art, or, may be bent into a "j-hook" design by the clinician prior to the interventional procedure.

With particular reference to FIGS. 3-5 and 10-12, remote segment 20 is shown including a plurality of fingers 21. It is envisioned that the inclusion of fingers 21 on remote segment 20 helps transmit torque applied by actuator 12 to leading end segment 18, without significantly impacting the flexibility of leading end segment 18.

Figure 4:
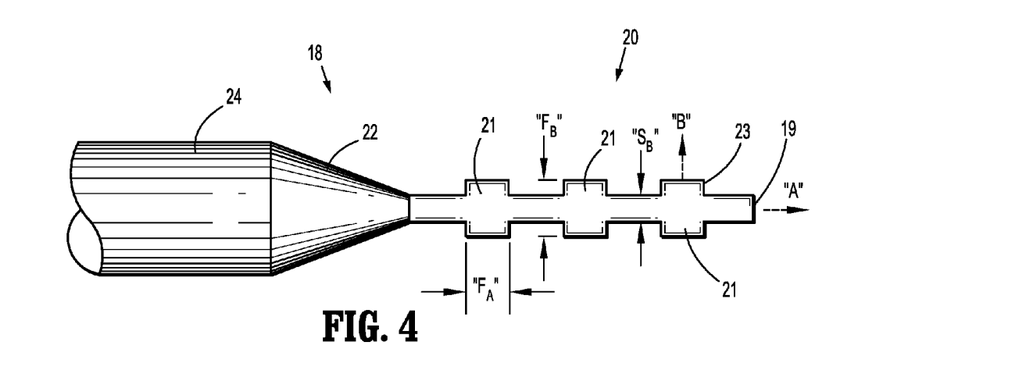
FIG. 4 is a plan view of a portion of the leading end segment of the guide member of the guidewire of FIGS. 1-3.
Figure 5:
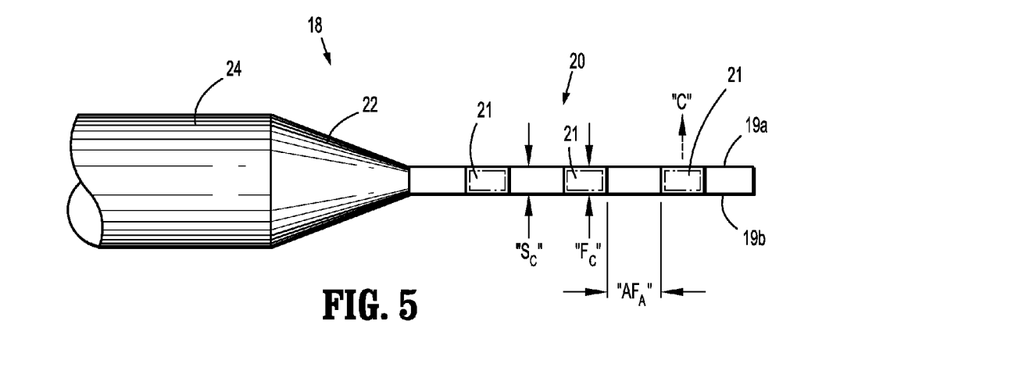
FIG. 5 is an elevation view of a portion of the leading end segment of the guide member of the guidewire of FIGS. 1-4.

In the embodiment illustrated in FIGS. 3-5, leading end segment 18 of guide member 14 includes a plurality of fingers 21 thereon. Each finger 21 defines a first transverse dimension "$F_B$" along a first transverse axis "B" (i.e., transverse to longitudinal axis "A"), a second transverse dimension "$F_C$" along a second transverse axis "C" (i.e., transverse to longitudinal axis "A" and perpendicular to longitudinal axis "B"), and a longitudinal dimension "$F_A$" along the longitudinal axis "A." Additionally, leading end segment 18 defines a first transverse dimension "$S_B$" along the first transverse axis "B," and a second transverse dimension "$S_C$" along the second transverse axis "C."

Figure 11:
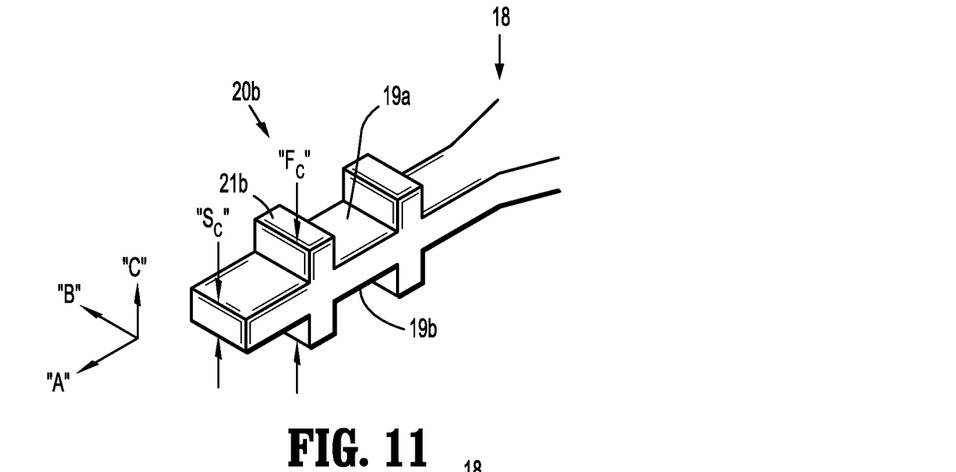
Figure 12:
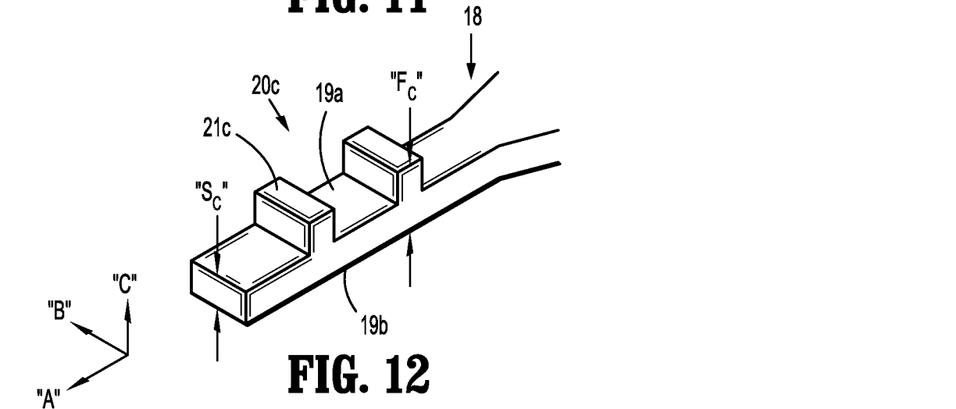

In the embodiment illustrated in FIGS. 3-5, remote segment 20 of leading end segment 18 includes three fingers 21, which are all identically sized, shaped and axially spaced apart from adjacent fingers 21. The present disclosure also contemplates more or fewer than three fingers 21 (e.g., two fingers as shown in FIGS. 11 and 12), and fingers 21 that differ in size, shape and/or spacing from adjacent fingers 21. Additionally, while fingers 21 are shown extending through a radial center of remote segment 20 of leading end segment 18, at least one finger 21 may extend along an upper surface 19a or a lower surface 19b of remote segment 20.

Additionally, and as particularly shown in FIGS. 2-4 and 6, first transverse dimension "$F_B$" of finger 21 is greater than the corresponding first transverse dimension "$S_B$" of remote segment 20 of leading end segment 18 (i.e., the portion of leading end segment 20 that finger 21 is in contact with). In disclosed embodiments, the distance "$F_B$" is between about 0.002 inches and about 0.004 inches, for example. It is also disclosed that the distance "$S_B$" is between about 0.001 inches and about 0.002 inches. Further, it is envisioned that the ratio between "$F_B$" and "$S_B$" is about 2:1. In disclosed embodiments, the distance "$F_A$" is between about 0.003 inches and about 0.025 inches, and the distances "$F_C$" and "$S_C$" are between about 0.001 inches and about 0.005 inches. Further, it is envisioned that the distances "$F_C$" and "$S_C$" are equal to one another. It is further disclosed that a distance "$AF_A$" between adjacent fingers 21 is between about 0.010 inches and about 0.100 inches. Additionally, it is envisioned that a distal edge 23 of a distal-most finger 21 is between about 0.000 inches and about 0.100 inches from a distal-most tip 19 of leading end segment 18. As can be appreciated, the distances provided herein are examples and are not intended to be limited to the disclosed ranges.

Figure 10:
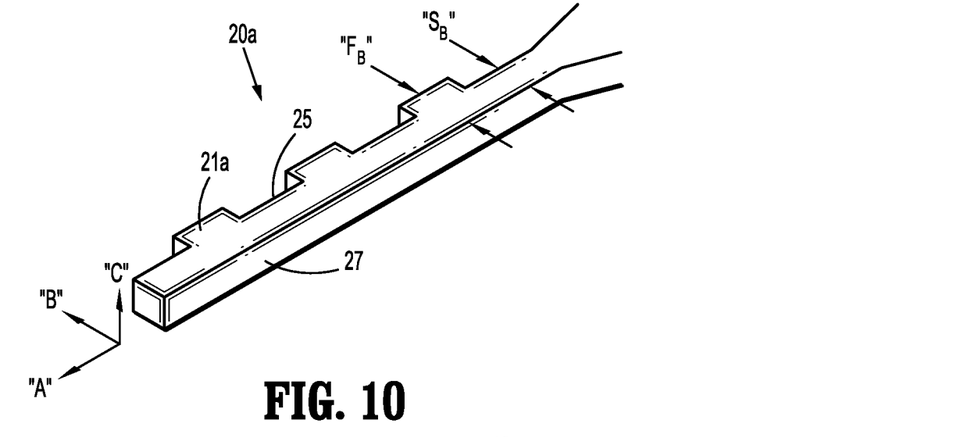
FIGS. 10-12 are perspective views of the leading end segment of the guide member according to embodiments of the present disclosure.

With reference to FIGS. 10-12, alternate embodiments of remote segment 20 are shown, and are indicated by reference numbers 20a, 20b, and 20c, respectively. In FIG. 10, remote segment 20a includes three fingers 21a. As shown, the first transverse dimension "$F_B$" of each finger 21a is greater than the corresponding first transverse dimension "$S_B$" of remote segment 20a of leading end segment 18 (i.e., the portion of leading end segment 20a that finger 21a is in contact with). Additionally, fingers 21a only extend beyond one lateral edge 25 of remote segment 20a; fingers 21a are flush with lateral edge 27.

Referring to FIGS. 11 and 12, remote segments 20b and 20c are shown, with each remote segment 20b and 20c including two fingers 21b and 21c, respectively. As shown, second transverse dimensions "$F_C$" of each finger 21b and 21c is greater than the corresponding second transverse dimension "$S_C$" of remote segment 20b and 20c, respectively. Additionally, fingers 21b extend beyond upper surface 19a and lower surface 19b (e.g., lateral surfaces) of remote end segment 20b, and fingers 21c only extend beyond upper surface 19a of remote segment 20c; fingers 21c are flush with lower surface 19b.

It is further envisioned that at least one finger 21 and/or remote segment 20 includes a transverse cross-sectional shape other than the rectangular cross-sections shown. For instance, finger 21 and/or remote segment 20 of leading end segment 18 can include any a circular, oval, or other polygon-shaped transverse cross-section.

A method of manufacturing a surgical guidewire 10 is also disclosed. The method includes forming guide member 14 such that guide wire 14 includes the features as described above. The disclosed methods include making leading end segment 18 (e.g., remote section 20) and fingers 21 of the same material (e.g., stainless steel, MP35N (a nickel-cobalt alloy), nitinol, or CoCr (a cobalt chromium alloy)), and include monolithically forming leading end segment 18 according to well known processes such as die stamping or micromachining (e.g., remote section 20) and fingers 21. It is also envisioned that leading end segment 18 and fingers 21 are made of different materials.

With continued reference to FIGS. 2 and 6-8, leading end segment 18 further includes at least one coil coaxially mounted about at least a portion of the leading end segment 18, and is mounted within outer sheath 42. In the embodiment, two coils are included, namely, first or proximal coil segment 44 and second or distal coil segment 46 forward of the proximal coil segment 44. Proximal coil segment 44 may be fabricated from a number of suitable materials. Proximal coil segment 44 may be dimensioned to extend to encompass second annular segment 28 and a portion of second tapered segment 26. The diameter of the wire of proximal coil segment 44 may range from about 0.0009 inches to about 0.0025 inches, and, in one embodiment, is about 0.0012 inches. Proximal coil segment 44 may also have a rectangular or flattened cross-section.

Figure 6:
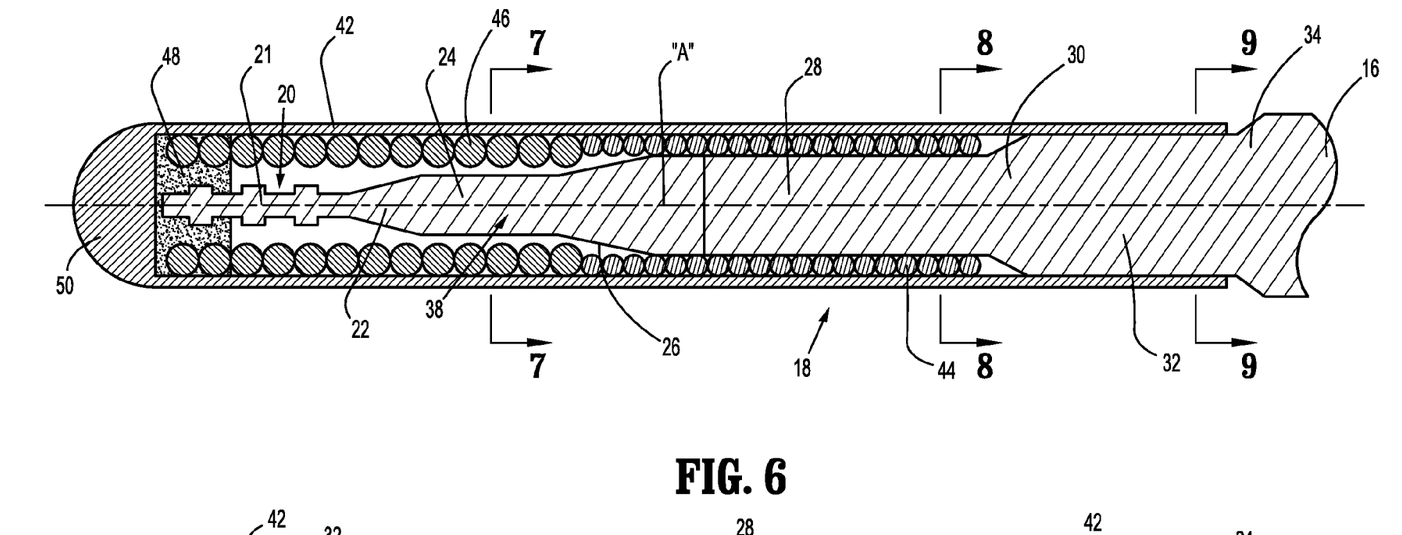
FIG. 6 is a longitudinal cross-sectional view of the guidewire of FIG. 2.

Distal coil segment 46 extends from proximal coil segment 44 and encompasses the remainder of leading end segment 18 of guide member 14. Distal coil segment 46 may be fabricated from a number of suitable materials, including, for example, stainless steel, MP35N™ (a nickel-cobalt alloy), nitinol, or CoCr (a cobalt chromium alloy). The wire of distal coil segment 46 has a diameter greater than the wire of proximal coil segment 44. In one embodiment, the diameter of distal coil segment 46 ranges from about 0.0012 inches to about 0.0025 inches, and may be about 0.0015 inches. Distal coil segment 46 may also have a rectangular or flattened cross-section. The radiopacity of distal coil segment 46 may assist in placement of leading end segment 18 within the vasculature through the use of imaging means, e.g., fluoroscopically during the interventional procedure.

Proximal coil segment 44 and distal coil segment 46 may provide lateral and/or torsional support to leading end segment 18. In one embodiment, the lateral strength (or resistance to bending) of distal coil segment 46 is less than the lateral strength of proximal coil segment 44 to permit flexing of a distal portion 38 of leading end segment 18. The outer diameters of proximal and distal coil segments 44, 46 may approximate each other and may be substantially equivalent to the diameter of third annular segment 32 to provide a smooth transition. The configurations of proximal and distal coil segments 44, 46 may be changed to provide varied properties if desired. In an embodiment, proximal and distal coil segments 44, 46 may be wound or otherwise disposed about leading end segment 18 in differing or opposite directions. In embodiments, adjacent turns of the coils of each of proximal and distal coil segments 44, 46 are in contacting relation (i.e., they are devoid of spacing between the adjacent coil turns). In one embodiment, proximal and distal coil segments 44, 46 may be joined at their interface. In addition, proximal and distal coil segments 44, 46 may be attached to leading end segment 18 of guide member 14 along various locations. Attachment may be effected though the use of adhesives, welding, soldering or the like. Distal coil segment 46 may be operatively connected or secured to leading end segment 18 through a soldering process or with the use of an adhesive such as an epoxy, cyanoacrylate adhesive or an ultraviolet (UV) light curable adhesive. The soldering or adhesive element is represented schematically as element 48 in FIG. 3.

Outer sheath 42 encloses leading end segment 18, and proximal and distal coil segments 44, 46. Outer sheath 42 may be fabricated from any suitable material, including, for example, polyurethanes, polyolefins, polyesters. In one embodiment, outer sheath 42 is a polyurethane sleeve which may or may not be loaded with tungsten, e.g., in microbead form. If loaded with tungsten, outer sheath 42 provides an additional element of radiopacity to leading end segment 18 of guide member 14. Outer sheath 42 may be thermoformed over leading end segment 18, and proximal and distal coil segments 44, 46 through conventional thermoform techniques. Outer sheath 42 defines an atraumatic arcuate leading end surface 50 to minimize the potential of trauma or abrasion of the vessel walls. In one embodiment, the diameter of outer sheath 42 is less than the diameter of proximal or trailing end segment 16 of guide member 14 to provide a smooth transition between the components.

The Table provided below identifies ranges of dimensions of the components of the leading end segment 18 for various guidewire sizes in accordance with the principles of the present disclosure. In the Table, D is represented as a percentage (%) of the diameter of the trailing end segment 16 and L represents the specific length of the component. For example, the diameter of first annular segment 24 may range from about 10% to about 30% of the diameter of trailing end segment 16 and have a length ranging from about 2 cm to about 10 cm. All ranges are approximate. Preferred dimensions for the specific guidewire sizes may be at the midpoint of the specified ranges. Variations of these dimensions are envisioned.

TABLE

|       | 1st Annular Segment 24 | 2nd Annular Segment 28 | 3rd Annular Segment 32 |
|-------|------------------------|------------------------|------------------------|
| D (%) | 10-30%                 | 25-50%                 | 50-90%                 |
| L (cm)| 2-10                   | 5-30                   | 10-30                  |

It is further envisioned that a lubricious coating may be disposed over components of guide member 14 including outer sheath 42. Suitable lubricious coatings include hydrophilic materials such as polyvinylpyrrolidone (PVP), polyethylene oxide, polyethylene glycol, cellulosic polymers, and hydrophilic maleic anhydride, or hydrophobic materials such as silicone, PTFE, or FEP. These coatings are typically applied by dip coating or spray methods, and heat curing may be used. For example, cure temperatures up to about 70 degrees C. are used for silicone coatings, and several hundred degrees may be required for PTFE coatings. In addition to the lubricious coating, bioactive coatings may be applied over all or part of the guidewire. Such coatings also may incorporate materials such as heparin, hirudin and its analogs, or other drugs. These coatings typically are applied by dip coating. Bioactive coatings are desirable to prevent blood clotting or for delivery of drugs to a specific site.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A guidewire comprising:
   an elongate guide member defining a longitudinal axis and having trailing and leading end segments, the leading end segment dimensioned for positioning within a body vessel, the leading end segment including a remote segment having a reduced cross-sectional dimension relative to a cross-sectional dimension of the trailing end segment, the remote segment including a pair of lateral sides extending along the longitudinal axis; and
   at least two fingers disposed on the remote segment, adjacent fingers being axially spaced relative to the longitudinal axis to define a predetermined distance therebetween, a first transverse dimension of each of the at least two fingers being greater than a corresponding first transverse dimension of the remote segment in contact therewith such that each of the at least two fingers project laterally beyond both of the lateral sides of the remote segment, the at least two fingers each defining a longitudinal dimension along the longitudinal axis less than the predetermined distance between the at least two fingers.

2. The guidewire according to claim 1 wherein the at least two fingers include different first transverse dimensions.

3. The guidewire according to claim 1 wherein a second transverse dimension of each of the at least two fingers is substantially equal to a corresponding second transverse dimension of the remote segment.

4. The guidewire according to claim 1 wherein the leading end segment and the at least two fingers are made of the same material.

5. The guidewire according to claim 1 wherein a the first transverse dimension of each finger of the at least two fingers along the first transverse axis is between about 0.002 inches and about 0.004 inches.

6. The guidewire according to claim 5 wherein a the first transverse dimension of the remote segment along the first transverse axis is between about 0.001 inches and about 0.002 inches.

7. The guidewire according to claim 6 wherein a second transverse dimension of each finger of the at least two fingers along a second transverse axis is between about 0.003 inches and about 0.005 inches.

8. The guidewire according to claim 5 wherein the predetermined distance between the at least two fingers is between about 0.010 inches and about 0.030 inches.

9. The guidewire according to claim 1 wherein the ratio between the first transverse dimension of each of the at least two fingers along the first transverse axis and the first transverse dimension of the remote segment along the first transverse axis is about 2:1.

10. The guidewire according to claim 1 wherein the at least two fingers are each dimensioned to extend through a radial center of the leading end segment.

11. The guidewire according to claim 1 wherein the remote segment defines a polygonal cross-section.

12. The guidewire according to claim 11 wherein the at least two fingers each define a polygonal cross-section.

13. The guidewire according to claim 1 wherein a distal-most end of the distal-most finger is positioned proximally of a distal-most end of the remote segment.

14. The guidewire according to claim 1 wherein the leading end segment and the at least two fingers are monolithically formed.

15. The guidewire according to claim 1 further comprising an intermediate segment positioned between the remote segment and the trailing end segment, the intermediate segment having a cross-sectional dimension that is larger than the cross-sectional dimension of the remote segment and that is smaller than the cross-sectional dimension of the trailing end segment.

16. A method for manufacturing a guidewire dimensioned for insertion within a body vessel of a subject, the method comprising:
    forming a guide member defining a longitudinal axis and having trailing and leading end segments, the leading end segment including a remote segment having a reduced cross-sectional dimension relative to a cross-sectional dimension of the trailing end segment, the remote segment including a plurality of fingers, adjacent fingers being disposed in axial spaced relation at a predetermined axial distance, a first transverse dimension of each finger being greater than a corresponding first transverse dimension of the remote segment in contact therewith, each finger defining a longitudinal dimension along the longitudinal axis less than the predetermined distance between the adjacent fingers; and
    at least one coil mounted about at least the remote segment.

17. The method of claim 16 wherein the step of forming includes stamping the remote segment and the at least one finger.

18. The method of claim 16 wherein the step of forming includes micro machining the remote segment and the at least one finger.

19. The guidewire according to claim 12 wherein the at least two fingers each define a general rectangular cross-section transverse to the longitudinal axis.

20. The guidewire according to claim 16 wherein each finger define a general rectangular cross-section transverse to the longitudinal axis.

21. A medical guidewire comprising:
    an elongate guide member defining a longitudinal axis and having proximal and distal end segments, the distal end segment including a reduced cross-sectional dimension relative to a cross-sectional dimension of the proximal end segment, the distal segment dimensioned for positioning within a body lumen; and
    at least three fingers disposed along the distal end segment, adjacent fingers being spaced along the longitudinal axis to define a predetermined distance therebetween, each finger defining first and second transverse dimensions, the first transverse dimension of each finger being greater than a corresponding first transverse dimension of the distal end segment in contact therewith such that each finger extends beyond lateral edges of the distal end segment, each finger defining a longitudinal dimension along the longitudinal axis less than the predetermined distance between adjacent fingers.

22. The guidewire according to claim 21 wherein adjacent fingers of the at least three fingers are axially spaced along the longitudinal axis at the same distance.

23. The guidewire according to claim 21 wherein adjacent fingers of the at least three fingers are axially spaced along the longitudinal axis at different distances.

24. The guidewire according to claim 21 wherein the at least fingers define a general rectangular shape in plan view.

25. The guidewire according to claim 21 wherein the distal end segment defines a distal tip, and the at least three fingers includes a distalmost finger, the distalmost finger being proximally spaced from the distal tip.

26. The guidewire according to claim 25 including at least one coil coaxially mounted about the leading end segment.

27. The guidewire according to claim 26 including an outer sheath enclosing the at least one coil.

28. The guidewire according to claim 21 wherein each finger defines a first transverse dimension greater than a second transverse dimension.

29. The guidewire according to claim 28 wherein each finger and the distal end segment each define a general rectangular cross-section transverse to the longitudinal axis.

* * * * *